US00PP08944P

United States Patent [19]

Olesen et al.

[11] Patent Number: Plant 8,944

[45] Date of Patent: Oct. 18, 1994

[54] MINIATURE ROSE PLANT NAMED 'POULCI'

[75] Inventors: Mogens N. Olesen; Pernille Olesen, both of Fredensborg, Denmark

[73] Assignee: Bear Creek Gardens, Inc., Medford, Oreg.

[21] Appl. No.: 97,165

[22] Filed: Jul. 23, 1993

[51] Int. Cl.[5] ..... A01H 5/00

[52] U.S. Cl. ..... Plt./9

[58] Field of Search ..... Plt. 7.1, 9

*Primary Examiner*—Howard J. Locker

*Attorney, Agent, or Firm*—Klarquist Sparkman Campbell Leigh & Whinston

[57] ABSTRACT

A rose plant of the miniature class, a sport of the variety POULvic, having a different flower color from its parent.

1 Drawing Sheet

The present invention relates to a new and distinct variety of rose plant of the miniature class which was discovered by us as a mutation of the variety POULvic, U.S. Plant Pat. No. 8,012.

This variety is unique and distinct from its parent variety, POULvic, principally in its flower color. Instead of having petals that are of Red Group 45C color, the petals are Red Group 56C on their upper sides and Red Group 56A on their reverse sides.

Asexual reproduction of this new variety by softwood cuttings, as performed at Somis, Calif., and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

FLOWER

Observations made from specimens grown in a greenhouse environment at Fredensborg, Denmark, in 1989.

Blooming habit: Continuous.

Bud:

*Size.*—1.6 cm long when the petals start to unfurl.

*Form.*—Pointed ovoid.

*Color.*—When sepals first divide, bud color is Red Group 56C. When half blown, the upper sides of the petals are Red Group 56C; and the lower sides of the petals are Red Group 56A.

*Sepals.*—Color: Reddish green. Surface texture: Covered in fine hairs. There are three normally appendaged sepals. There are two unappendaged sepals with hairy edges.

*Receptacle.*—Color: Green. Shape: Apple. Size: Small. Surface: Smooth.

*Peduncle.*—Length: Medium. Surface: Smooth. Color: Light green. Strength: Bending.

Bloom:

*Size.*—Small. Average open size is 3.5 cm in diameter.

*Borne.*—Several together, in rounded-to-flat clusters averaging 3 to 7 flowers.

*Stems.*—Medium (average length 15 to 18 cm); strong, for a pot rose.

*Form.*—When first open: High centered. Permanence: Flattens, outer petal edges slightly curled.

*Petalage.*—Number of petals under normal conditions: 30 to 40.

*Color.*—The upper side of the petals is Red Group 56C. The reverse side of the petals is Red Group 56A. The base of petals in White Group 155C. The major color on the upper side is Red Group 56C.

*Variegations.*—None, except on guard petals, where there is an occasional greenish streak.

*Discoloration.*—There is no change in general tonality at the end of the first day. At the end of the third day, there is a gradual lightening in color to Red Group 56D.

*Fragrance.*—Slight.

Petals:

*Texture.*—Leathery.

*Shape.*—Oval, pointed.

*Form.*—Tips slightly recurved.

*Arrangement.*—Imbricated, with few petaloids in the center.

*Persistence.*—Drop off cleanly.

*Lastingness.*—On the plant: Very long (10 to 15 days). As a cut flower: Very long (15 days).

Reproductive parts:

*Anthers.*—Size: Small. Quantity: Many. Color: Yellow. Arrangement: Regular around styles.

*Filaments.*—Color: White.

*Pollen.*—Color: Gold yellow.

*Styles.*—Color: White.

*Stigmas.*—Color: Yellow.

Form: Bush.

Growth: Dwarf. Maximum height as a pot rose is 20 to 25 cm.

Foliage:

*Number of leaflets on normal mid-stem leaves.*—5.

*Size.*—Small.

*Quantity.*—Abundant to normal.

*Color.*—New foliage: Green Group 138B. Reverse: Green Group 138C. Old foliage: Green Group 137A, slightly red on reverse.

Leaflets:

*Shape.*—Oval pointed.

*Texture.*—Upper side: Leathery.

*Edge.*—Serrated.

*Serration.*—Single, small.

*Petiole rachis.*—Color: Green.

*Petiole underside.*—Smooth.

*Stipules.*—Short, smooth, bearded.

*Disease resistance.*—Resistant to mildew under normal greenhouse conditions in Denmark and in Somis, Calif.

Wood:

*New wood.*—Color: Light green. Bark: Smooth.

*Old wood.*—Color: Green. Bark: Smooth.

Prickles:

*Quantity.*—Few on main canes from base and on laterals from main canes.

*Form.*—Short, straight.

*Color when young.*—Green at base shading to red at tip, quickly turning all green.

Small prickles:

*Quantity.*—Few on main stalks and on laterals.

*Color.*—Green.

We claim:

1. A new and distinct variety of rose plant of the miniature class, substantially as herein shown and described, a sport of the variety POULvic characterized particularly by its flower color difference from its parent.

* * * * *

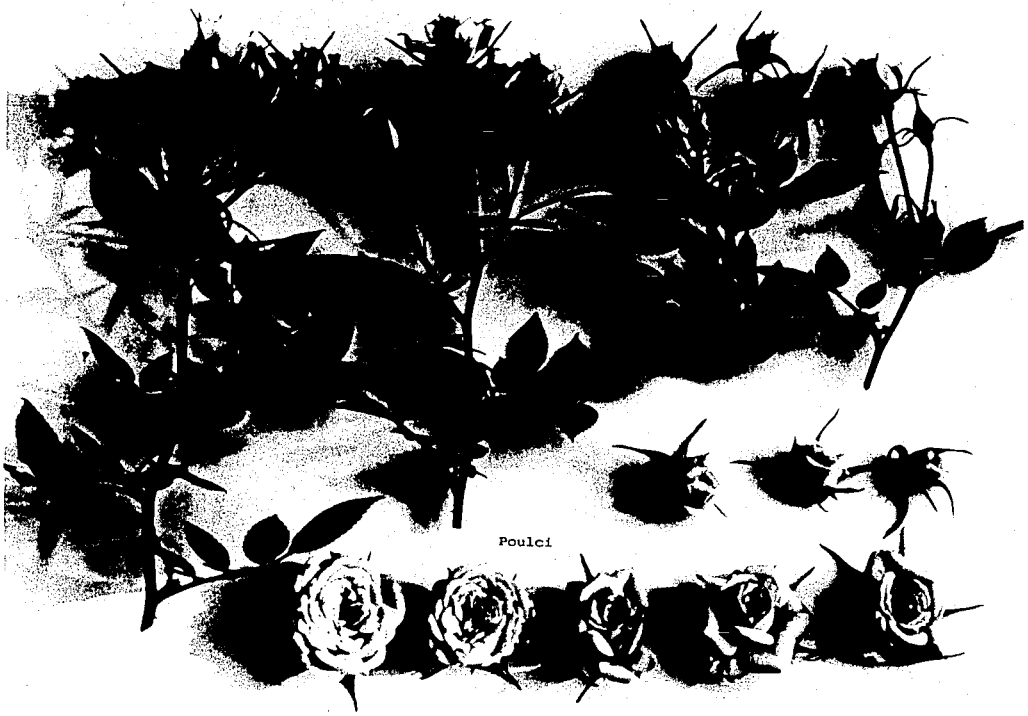
Poulci